(12) United States Patent
Kiefer et al.

(10) Patent No.: US 7,747,313 B2
(45) Date of Patent: Jun. 29, 2010

(54) METHOD FOR ACQUIRING DYNAMIC MAGNETIC RESONANCE SIGNALS FOR TOMOGRAPHY

(75) Inventors: Berthold Kiefer, Erlangen (DE); Niels Oesingmann, Buckenhof (DE); Alto Stemmer, Abenberg (DE)

(73) Assignee: Siemens Aktiengesellschaft, Munich (DE)

( * ) Notice: Subject to any disclaimer, the term of this patent is extended or adjusted under 35 U.S.C. 154(b) by 540 days.

(21) Appl. No.: 11/112,073

(22) Filed: Apr. 22, 2005

(65) Prior Publication Data

US 2005/0245813 A1    Nov. 3, 2005

(30) Foreign Application Priority Data

Apr. 22, 2004   (DE)   .................. 10 2004 019 590

(51) Int. Cl.
*A61B 5/05*   (2006.01)
(52) U.S. Cl. .................. 600/428; 600/410; 600/413
(58) Field of Classification Search .............. 600/410, 600/413, 428
See application file for complete search history.

(56) References Cited

U.S. PATENT DOCUMENTS

| | | | | |
|---|---|---|---|---|
| 5,926,021 | A * | 7/1999 | Hennig | 324/306 |
| 6,198,959 | B1 * | 3/2001 | Wang | 600/413 |
| 6,473,634 | B1 * | 10/2002 | Barni | 600/425 |
| 2002/0107443 | A1 * | 8/2002 | Stefancik et al. | 600/419 |
| 2002/0143246 | A1 * | 10/2002 | Hardy et al. | 600/410 |
| 2003/0023154 | A1 * | 1/2003 | Nitz | 600/407 |
| 2003/0088174 | A1 * | 5/2003 | Sussman et al. | 600/410 |

* cited by examiner

*Primary Examiner*—Long V Le
*Assistant Examiner*—Ellsworth Weatherby
(74) *Attorney, Agent, or Firm*—Schiff Hardin LLP

(57) ABSTRACT

In a method for acquiring dynamically varying magnetic resonance signals, a respiration cycle of a patient is monitored in a learning phase. Acquisition of varying signals ensues with the highest possible temporal resolution in an initial phase with a breath-hold by the patient. Slowly varying signals are subsequently acquired with lower temporal resolution in a movement phase and with free respiration of the patient. The signal acquisitions are initiated by a pre-established trigger condition.

10 Claims, 1 Drawing Sheet

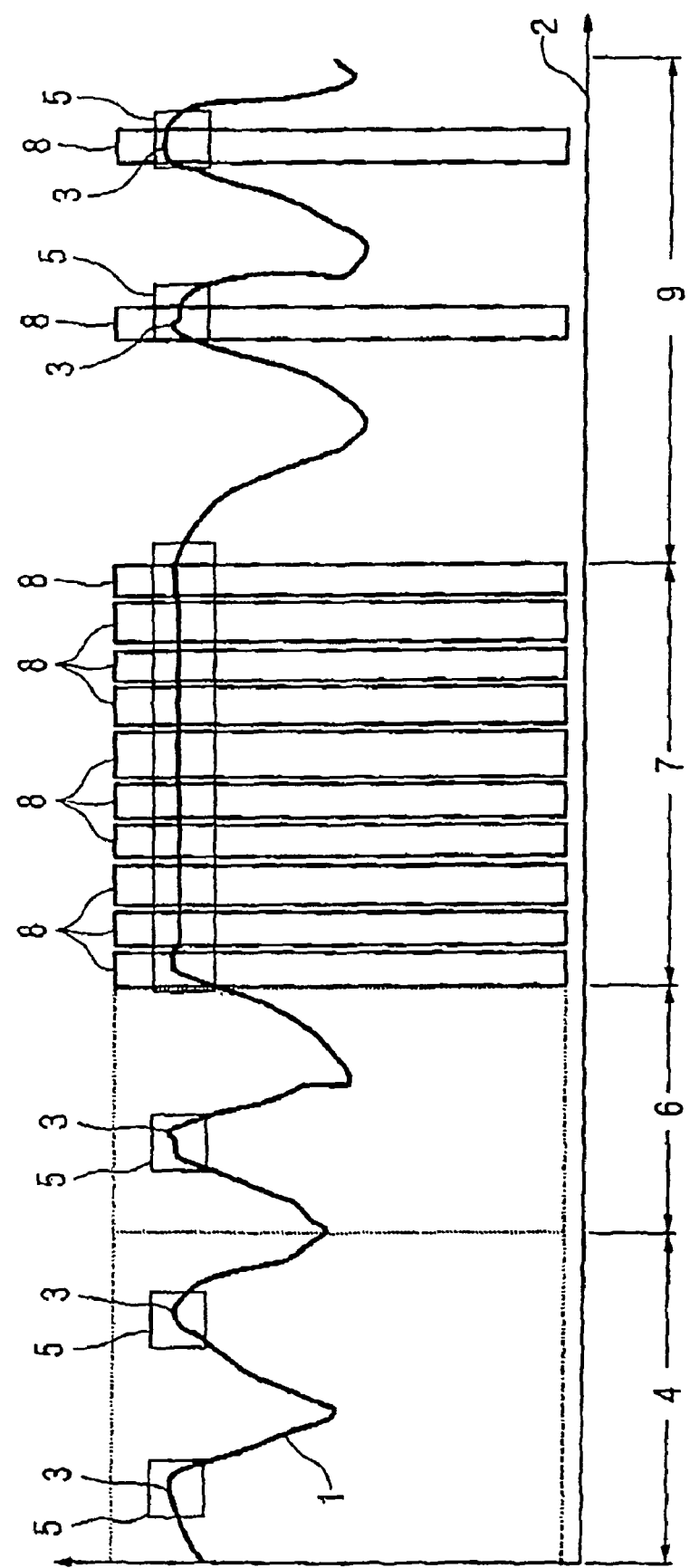

METHOD FOR ACQUIRING DYNAMIC MAGNETIC RESONANCE SIGNALS FOR TOMOGRAPHY

BACKGROUND OF THE INVENTION

1. Field of the Invention

The present invention concerns a method for acquiring dynamic magnetic resonance signals in magnetic resonance tomography.

2. Description of the Prior Art

Adaptation of the temporal resolution of the measurement of speeds of signal variations is necessary in the acquisition of dynamically varying magnetic resonance signals that are used to generate a tomographic image. Faster signal variations thus must be acquired with higher temporal resolution than slower varying signals. A fast signal change occurs, in particular shortly after the injection of a contrast agent into the subject, while the signals vary substantially slower after what is known as the first-pass effect, i.e., as soon as the contrast agent has, for example, passed the liver of a patient. It is desirable to adapt the temporal resolution to the speed of the signal variation during the signal acquisition. Moreover, as is always the case, unwanted signal variations (as are created, for example, by a movement or respiration of the patient) generate measurement artifacts and therefore must be compensated or prevented.

One possibility for reducing measurement artifacts due to movements or breathing by the patient is to implement the entire acquisition (scan) with the highest possible temporal resolution. Movements of an organ that are created due to breathing or movement of the patient then are not of importance during the acquisition of signals (data) for a single image since they ensue distinctly slower than the image acquisition. The influence of movement on a series of images is visible, however, such that in that case correction measures are necessary. In particular, in the case of movements perpendicular to the slice plane these correction measures are possible only with three-dimensional, with the temporal resolution being substantially clearly less for purely two-dimensional measurements. Additionally a large data quantity results due to the high temporal resolution, particularly for longer examinations.

Another possibility for preventing measurement artifacts due to breathing of the patient is to implement the measurement during a breath-hold by the patient. The signal is acquired with the highest possible temporal resolution during the breath-hold. However, after a relatively short scan duration a pause is necessary so that the patient can breath again. It is nearly impossible to repeat the scan with the patient in the identical respiratory position as before, during a subsequent breath-hold by the patient. Elaborate correction methods are in turn necessary for compensation of the different respiratory positions respectively in successive scans.

Furthermore, it is possible to acquire the breathing motion (for example using a navigator echo) in a discrete measurement and to use it for correction of the actual measurement data. This method requires a high time expenditure because the breathing motion must be acquired in a separate measurement. Moreover, it is difficult to correct the complex three-dimensional movement of the organs during a breathing cycle.

Furthermore, it is possible to combine various methods. Thus the quickly varying signals can be acquired first with the highest possible temporal resolution during a breath-hold by the patient, and after this the slowly varying signals are acquired during free respiration of the patient. In principle the same difficulties explained above still occur particularly during the signal acquisition during free respiration.

SUMMARY OF THE INVENTION

An object of the present invention to provide a method for acquiring dynamically varying (changing) magnetic resonance signals in which both rapidly varying and slowly varying signals are acquired and the measurement artifacts are minimized.

This object is achieved in accordance with the invention by a method wherein, in an initial phase, the varying signal is acquired with the highest available temporal resolution and in a subsequent movement phase of the scan, a physiological event of the patient is automatically acquired and the varying signal is acquired further. The acquisition during the movement phase is related to the physiological event, for example respiration of the patient. As already described, in known methods problems occur due to measurement artifacts in the acquisition of signals with varying dynamics that, for example, initially vary rapidly and subsequently vary slowly. In the inventive method, the specified combination of the two measurement phases for the different signal variations produces a decisive reduction of the measurement artifacts compared to known measurement methods. For example, during the initial phase the rapidly varying signal is measured with the highest possible temporal resolution and the slowly varying signal is measured in the subsequently movement phase. A further advantage of the inventive method in which signal acquisition occurs continuously only with the maximal temporal resolution is a significantly reduced data quantity, because an unnecessarily large number of images, which may not be necessary for the diagnosis are not acquired in the acquisition of the slowly-varying signals.

In an embodiment of the method, after a pre-established number of signal acquisitions during the initial phase the physiological event is automatically analyzed in the movement phase. Acquisition of measurement data thereby ensues only during a specific part of the physiological event, for example the respiration of the patient. The acquisition is initiated by a pre-established trigger condition, for example a breathing position advantageous for the acquisition of the measurement data. Due to the established trigger condition, the organs to be examined are located in nearly the same position for each acquisition of measurement data, such that measurement artifacts are prevented as much as possible.

The ability to change the trigger condition during the movement phase can be integrated into the method. This allows adjustment to variations of the physiological event that occur during the measurement procedure.

In a further embodiment, a learning phase is provided before the initial phase of the measurement procedure, during which learning phase the physiological event is acquired and analyzed and the trigger condition is adapted. The trigger condition is thereby adjusted to the respective patient and his or her physiological event in each measurement procedure.

A further embodiment of the method includes the injection of a contrast agent at the end of a start phase that temporally lies between the learning phase and the initial phase. The measurement of the fast signal variations resulting from the injection begins immediately after this injection, in the initial phase. An optimal imaging of the signal variations caused by migration or perfusion of the contrast agent is thus possible.

A physiological event that is particularly suitable for monitoring is breathing of the patient. In an embodiment, breathing is monitored and a selected respiratory position, preferably end expiration, is defined as the trigger condition. The monitoring of the respiration can ensue, for example, using a navigator echo or a respiration belt. The method, however, is not limited to breathing as the physiological event. For example, a cardiac rhythm also can be used as a physiological event.

Acquisition of the fast signal variations during the initial phase advantageous ensues during a breath-hold by the patient. Movement artifacts are thus prevented during this phase of the measurement procedure.

The known methods for correction of measurement artifacts can advantageously be combined with the inventive method in order to correct small measurement artifacts that may possibly remain.

DESCRIPTION OF THE DRAWINGS

The FIGURE shows a schematic representation of a magnetic resonance signal acquisition procedure according to the inventive method.

DESCRIPTION OF THE PREFERRED EMBODIMENTS

In the FIGURE, the respiration cycle of a patient is plotted as a line 1 against a time axis 2. The maxima 3 of the respiration cycle here represent the exhaled state of the patient. The respiration cycle is acquired during a learning phase 4 and the corresponding movement is tracked, and the trigger condition 5 marked in the FIGURE is established. In a start phase 6, the patient receives an instruction to hold his or her breath in the exhaled state after one and a half respiration cycles. An injection of contrast agent simultaneously ensues. In a subsequent initial phase 7, a quickly varying magnetic resonance signal is acquired with the highest-available temporal resolution during the breath-hold. The acquisition of a single image is indicated by a rectangle 8. The respiration curve is not shown. After ten measurement events, monitoring of the breathing is automatically begun, and in a movement phase 9 the acquisition 8 of a single image is automatically triggered by the trigger condition 5 with free respiration of the patient. This then ensues continuously during each respiration cycle. The acquisition of an image respectively ensues in the exhaled state of the patient, since then the ability to reproduce the position of the organs to be examined is greatest.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for acquiring dynamic magnetic resonance signals for magnetic resonance tomography, comprising the steps of:

in an initial phase of a signal acquisition procedure, acquiring a varying magnetic resonance signal from a subject with a highest available temporal resolution, with substantially no movement of the subject occurring in said initial phase;

in a subsequent movement phase of said signal acquisition procedure, entirely following said initial phase, automatically acquiring a signal representing a physiological event of the subject having exterior movement of the subject associated therewith;

in said movement phase, also acquiring said varying magnetic resonance signal from the subject, but at less than said highest available temporal resolution relative to an entirety of said movement phase; and relating the varying magnetic resonance signal acquired during said movement phase to said physiological event.

2. A method as claimed in claim 1 comprising making a plurality of signal acquisitions of said dynamic magnetic resonance signal in said initial phase, and automatically transitioning, in said signal acquisition procedure, from said initial phase to said movement phase after a predetermined number of said signal acquisitions.

3. A method as claimed in claim 1 comprising acquiring said varying magnetic resonance signal in said movement phase dependent on a pre-established trigger condition.

4. A method as claimed in claim 1 comprising acquiring said varying magnetic signal in said movement phase dependent on a trigger condition, and allowing changing of said trigger condition during said movement phase.

5. A method as claimed in claim 1 comprising, in a learning phase of said signal acquisition procedure preceding said initial phase, also acquiring said signal representing said physiological event, and analyzing said signal representing said physiological event to establish a trigger condition and, in said movement phase, acquiring said varying magnetic resonance signal dependent on said trigger condition.

6. A method as claimed in claim 5 comprising, in a start phase of said signal acquisition procedure between said learning phase and said initial phase, injecting a contrast agent into the subject.

7. A method as claimed in claim 1 wherein the step of automatically acquiring a signal representing a physiological event of the subject comprises automatically acquiring a signal representing respiration of the subject.

8. A method as claimed in claim 7 comprising, in said initial phase, acquiring said varying magnetic resonance signals from the subject during a breath-hold by the subject.

9. A method as claimed in claim 8 comprising, in a start phase of said signal acquisition procedure preceding said initial phase, injecting a contrast agent into the subject and, after a predetermined number of respiration cycles by the subject, instructing the subject to begin said breath-hold.

10. A method as claimed in claim 1 comprising generating magnetic resonance data from the acquired varying magnetic resonance signals and generating an image of the subject from said magnetic resonance data, and subjecting said magnetic resonance data to a motion correction procedure to remove movement artifacts from said image.

* * * * *